(12) United States Patent
Graumann

(10) Patent No.: US 9,039,283 B2
(45) Date of Patent: May 26, 2015

(54) METHOD AND APPARATUS FOR PRODUCING AN X-RAY PROJECTION IMAGE IN A DESIRED DIRECTION

(71) Applicant: Siemens Aktiengesellschaft, München (DE)

(72) Inventor: Rainer Graumann, Hoechstadt (DE)

(73) Assignee: Siemens Aktiengesellschaft, Munich (DE)

(*) Notice: Subject to any disclaimer, the term of this patent is extended or adjusted under 35 U.S.C. 154(b) by 243 days.

(21) Appl. No.: 13/649,629

(22) Filed: Oct. 11, 2012

(65) Prior Publication Data

US 2013/0089180 A1    Apr. 11, 2013

(30) Foreign Application Priority Data

Oct. 11, 2011   (DE) .......................... 10 2011 084 279

(51) Int. Cl.
*A61B 6/08* (2006.01)
*A61B 6/00* (2006.01)

(52) U.S. Cl.
CPC ................ *A61B 6/08* (2013.01); *A61B 6/4441* (2013.01); *A61B 6/547* (2013.01)

(58) Field of Classification Search
USPC ........................................................ 378/205
See application file for complete search history.

(56) References Cited

U.S. PATENT DOCUMENTS

| 4,356,400 | A | * | 10/1982 | Polizzi et al. ................. 378/138 |
| 5,031,203 | A | * | 7/1991 | Trecha .......................... 378/205 |
| 6,002,743 | A | * | 12/1999 | Telymonde ................... 378/98.8 |
| 8,165,660 | B2 | * | 4/2012 | Pfister et al. .................. 600/427 |
| 2004/0006850 | A1 | * | 1/2004 | Wax ............................... 24/10 R |
| 2009/0274271 | A1 | * | 11/2009 | Pfister et al. ..................... 378/62 |
| 2009/0278702 | A1 |   | 11/2009 | Graumann et al. |

FOREIGN PATENT DOCUMENTS

| DE | 102007029199 A1 | 1/2009 |
| DE | 102008022921 A1 | 11/2009 |

* cited by examiner

*Primary Examiner* — Phillip A Johnston
(74) *Attorney, Agent, or Firm* — Laurence A. Greenberg; Werner H. Stemer; Ralph E. Locher

(57) ABSTRACT

A method for producing an X-ray projection image of a body region of a patient using a desired spatial location of a central ray, includes positioning a pointing element relative to the patient indicating a location of a pointing line and causing the location of the pointing line to coincide with the desired central ray location. A pointing line location and a central ray location currently set on an X-ray machine are recorded. A measure for deviation between the pointing line and the currently set central ray location is determined and used to set the desired central ray location. A medical apparatus includes an X-ray machine taking an X-ray projection image along a central ray, a pointing element indicating a pointing line, an acquisition unit detecting the pointing line location and the currently set central ray location, and a control and evaluation unit implementing software carrying out the method.

15 Claims, 2 Drawing Sheets

METHOD AND APPARATUS FOR PRODUCING AN X-RAY PROJECTION IMAGE IN A DESIRED DIRECTION

CROSS-REFERENCE TO RELATED APPLICATION

This application claims the priority, under 35 U.S.C. §119, of German Patent Application DE 10 2011 084 279.9, filed Oct. 11, 2011; the prior application is herewith incorporated by reference in its entirety.

BACKGROUND OF THE INVENTION

Field of the Invention

The invention relates to a method for producing an X-ray projection image of a body region of a patient using a desired spatial location of a central ray. The invention also relates to a medical apparatus for carrying out the method. The location denotes the position, i.e. the point of entry, and the orientation, i.e. the direction.

In medicine, X-ray projection images of particular areas of the body, i.e. a selected body region, of a patient are often obtained for diagnosis and treatment. An X-ray scan is intended not only to show the selected area, but also to show it from a particular angle, i.e. from a particular or desired direction, so that the body region appears in the desired manner. In order to achieve that, the X-ray machine must be positioned correctly, namely in such a way that the central ray of the X-ray machine is incident on the patient from a desired direction and at a desired position.

It is known to position the X-ray machine with a desired location of the central ray by incremental approximation: the X-ray machine is moved to a first position and then a first X-ray scan is taken. That first scan enables the location of the body region in the image to be identified. The X-ray machine can then be suitably aligned by eye, or more specifically the location of the central ray can be readjusted accordingly. It is often necessary to repeat that step several times until the desired image segment is captured in the desired orientation. That iterative positioning process is therefore very time-consuming. In addition, it is often difficult to formulate instructions for the clinical staff as to the direction in which the X-ray machine is to be moved or rotated in such a way that they can be carried out precisely and without misunderstanding. Moreover, the X-rays taken for positioning the X-ray machine prior to the actual examination unnecessarily increase the patient's radiation exposure.

SUMMARY OF THE INVENTION

It is accordingly an object of the invention to provide an improved method for producing an X-ray projection image of a body region of a patient in a desired direction using a desired spatial location of a central ray and a medical apparatus for carrying out the method, which overcome the hereinafore-mentioned disadvantages of the heretofore-known methods and apparatuses of this general type.

With the foregoing and other objects in view there is provided, in accordance with the invention, a method for producing an X-ray projection image of a selected body region of a patient using a desired spatial location of a central ray. The method comprises initially indicating the desired location of the central ray using a pointing element indicating a pointing line and then recording the location of the pointing line with an acquisition unit. Through the use of the current location of the central ray and the location of the pointing line, i.e. the desired location of the central ray, a control and evaluation unit determines a measure for the deviation and makes this measure available for setting the desired location of the central ray or more specifically the desired position and orientation of the X-ray machine.

In a first step, a pointing element which indicates the location of a pointing line is positioned relative to the patient in such a way that the location of the pointing line coincides with the desired location of the central ray. In other words, the desired point of entry of the central ray into the patient and the desired direction of the central ray is predefined by the location of the pointing element or more precisely of the pointing line. The pointing element can be placed in a freely selectable manner anywhere and at any distance with respect to the patient, e.g. even directly onto the patient, thereby allowing flexible determination of the desired location of the central ray.

In a second step, the location of the pointing line and the location of the central ray currently set on the X-ray machine are recorded using an acquisition unit. In other words, the present position and orientation of the central ray and therefore also of the X-ray machine as well as the desired point of entry and the pointing direction defined by the pointing line are recorded.

In a final step, a measure for the deviation between the location of the pointing line and the currently set location of the central ray is determined. For this purpose e.g. a control and evaluation unit having suitably implemented software is present which determines a locational difference from the location of the pointing line and the location of the central ray currently set that have been recorded by the acquisition unit and provides that difference for further processing. In other words, the control and evaluation unit calculates a spatial difference value between the currently set and the desired central ray and outputs it in the form of a locational relationship and/or suitable coordinates. The measure for the deviation can then be used to set the desired location of the central ray. In other words, on the basis of the locational difference, the X-ray machine can be positioned in such a way that the position and orientation of the central ray coincides with the location of the pointing line, and a deviation between the two no longer exists.

The method according to the invention ensures that the X-ray machine can be correctly placed at the desired position in a desired orientation without needing to take prior X-ray projection images for setting the desired location of the central ray. This reduces the radiation exposure for the patient and the medical personnel and is less time-consuming than the iterative method mentioned in the introduction. The indication of the desired location of the central ray by the pointing element also simplifies instructions and the necessary communication between surgeon and medical staff for positioning the X-ray machine, thereby enabling the X-ray machine to be positioned without difficulty in a user-friendly manner. Thus, should coarse alignment of the X-ray machine be necessary, e.g. if the C-arm is too far from the desired position, the C-arm must be moved manually to approximately the desired position by the operating personnel.

In accordance with another preferred mode of the method of the invention, the measure for the deviation is output to a user through a user interface. For example, the currently set and the desired location of the central ray are also or alternatively indicated, likewise e.g. displacement and rotational directions are specified, in order to position the X-ray machine correctly. In other words, on the basis of the specified angular and/or directional deviations, the user can position the X-ray machine manually in such a way that the desired central ray is aligned with the pointing line.

In accordance with a further preferred mode of the method of the invention, the measure for the deviation is output as a control signal to a motor-adjustable X-ray machine. Thus, e.g. the desired location of the central ray can be automatically set.

In accordance with an added preferred mode of the method of the invention, the location of the currently set central ray is preferably indicated by a pointing element by positioning the same in such a way that a second pointing line coincides with the currently set location of the central ray. In other words, the present position and orientation of the central ray is thus determined by using the pointing element or more specifically the second pointing line.

In accordance with an additional preferred mode of the method of the invention, the pointing element is moved manually relative to the patient. This allows very simple placement of the pointing element and the associated defining of the location of the desired central ray, requiring no additional equipment complexity or time-consuming positioning of the pointing element itself. The necessary communication between the technical personnel involved for positioning the X-ray machine is likewise simplified, since the desired location of the central ray and therefore the position and orientation of the X-ray machine are clearly indicated.

In accordance with yet another preferred mode of the method of the invention, the pointing line is optically indicated, particularly in the range of visible light, e.g. using a pointer with optical marker. A basic concept resides, among other things, in recording the pointing element using video cameras mounted on the detector side and on the tube side as the acquisition unit. For this purpose, it is helpful if optical markers, e.g. colored lines, which can be recorded by the video cameras are provided on the pointing element. The location of the pointing element can then be determined therefrom.

An optically operating acquisition unit is preferably used, so that the location of the pointing line and the location of the currently set central ray can be acquired optically, mainly in the visible light region or in the infrared region. Optical acquisition can take place using a single camera and using a stereo camera. The specific nature of the markers would then be easily distinguishable. The one or more video cameras can be mounted e.g. both on the detector side and on the tube side, with known calibration in each case.

With the objects of the invention in view, there is also provided a medical apparatus for carrying out the method according to the invention. The medical apparatus comprises an X-ray machine, a pointing element, an acquisition unit and a control and evaluation unit.

In accordance with another feature of the medical apparatus of the invention, the X-ray machine which is used is preferably a C-arm X-ray machine, thereby enabling the X-ray machine to be moved in a simple manner and suitably positioned relative to the patient.

In accordance with a further preferred feature of the medical apparatus of the invention, the pointing element is implemented in the form or shape of a pencil so that the pointing line coincides with a longitudinal axis of the pencil.

In accordance with an added feature of the medical apparatus of the invention, the acquisition unit is preferably mounted directly on the X-ray machine, thus limiting the mutual registration of the coordinate systems of the acquisition unit and X-ray machine to a minimum and achieving maximum overlapping of the acquisition area with the projection area of the X-ray machine. However, the acquisition unit is calibrated in each case so that the transformation between the central ray and the main axis of the acquisition area for the respective position of the acquisition unit is known.

In accordance with an additional feature of the medical apparatus of the invention, as far as possible, the acquisition unit has an acquisition area which encompasses the projection area of the X-ray machine, i.e. where possible is larger than the latter.

In accordance with yet another feature of the medical apparatus of the invention, if an optically operating acquisition unit is used for carrying out the method according to the invention, this is implemented in particular by using optical cameras as the acquisition unit.

In accordance with a concomitant preferred feature of the medical apparatus of the invention, the acquisition unit includes a plurality of sub-units, the acquisition areas of which at least partially overlap, thereby increasing the accuracy in recording the location of the pointing line and currently set central ray.

Other features which are considered as characteristic for the invention are set forth in the appended claims.

Although the invention is illustrated and described herein as embodied in a method and an apparatus for producing an X-ray projection image in a desired direction, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
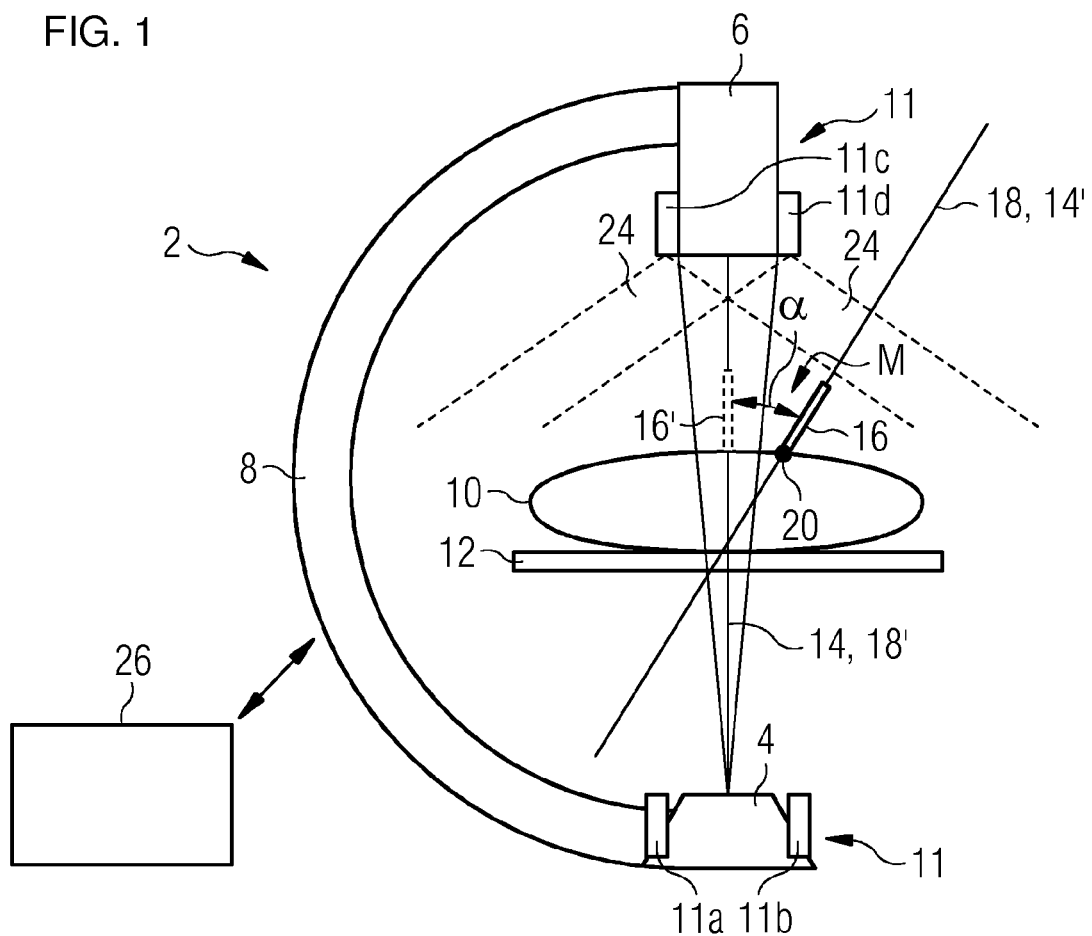
FIG. 1 is a diagrammatic, side-elevational view of a C-arm-X-ray machine in a first position in which a currently set central ray deviates from a desired location of the central ray.

Referring now to the figures of the drawings in detail and first, particularly, to FIG. 1 thereof, there is seen an X-ray machine 2 having an X-ray source 4 and an X-ray detector 6 which are both in turn mounted on ends of a support 8 that is implemented in this case as a C-arm. A diagrammatically represented patient 10 on a table 12 is located between the X-ray source 4 and the X-ray detector 6. The X-ray machine 2 takes X-ray projection images along a central ray 14 proceeding from the X-ray source 4 to the X-ray detector 6.

In FIG. 1, the X-ray machine 2 is in a first position, having a currently set position and orientation 30 (see FIG. 2) and a present location of the central ray 14. This is at variance with a desired location of the central ray 14' for capturing an X-ray projection image. In order to carry out the method, a pointing element 16, which is pencil-shaped in this example, is first moved relative to the patient 10 in such a way that an indicated pointing line 18 coincides with the desired location of the central ray 14'. The pointing line 18 therefore indicates the direction of the desired central ray 14' and also a desired position, i.e. a subsequent point of entry 20 of the central ray 14' into the patient 10. In the exemplary embodiment, the pointing element 16 is placed directly on the patient 10, i.e. at the point of entry 20. The location of the pointing line 18, i.e. the location of the desired central ray 14', deviates by a measure M, in this exemplary embodiment by an angle α, from the currently set location of the central ray 14.

In the next step, an acquisition unit 11 records the location of the pointing element 16 and therefore the location of the pointing line 18, the location of which relative to the pointing element 16 is known, as well as the currently set location of the central ray 14. The acquisition unit 11 in this case has a plurality of sub-units 11a to 11d with acquisition areas 24 which at least partially overlap. In this exemplary embodiment, the sub-units 11a-d are mounted directly on the X-ray machine 2, with two sub-units (11a, b) on the side of the X-ray source 4 and two sub-units (11c, d) on the side of the X-ray detector 6. As already mentioned, by using a plurality of sub-units, a higher accuracy in carrying out the method is achieved.

The acquisition unit 11 is calibrated, i.e. the location of the acquisition unit 11 and the acquisition area 24 thereof relative to the X-ray machine and the central ray are known. If the X-ray machine 2 is a C-arm-X-ray machine as in the example, and if the acquisition unit 11, as in this example, is mounted directly on the X-ray machine 2, during acquisition the C-arm deflection is taken into account using corresponding projection geometries.

A control and evaluation unit 26 then determines the measure M for the deviation between the location of the pointing line 18 and the currently set location of the central ray 14.

Figure 2:
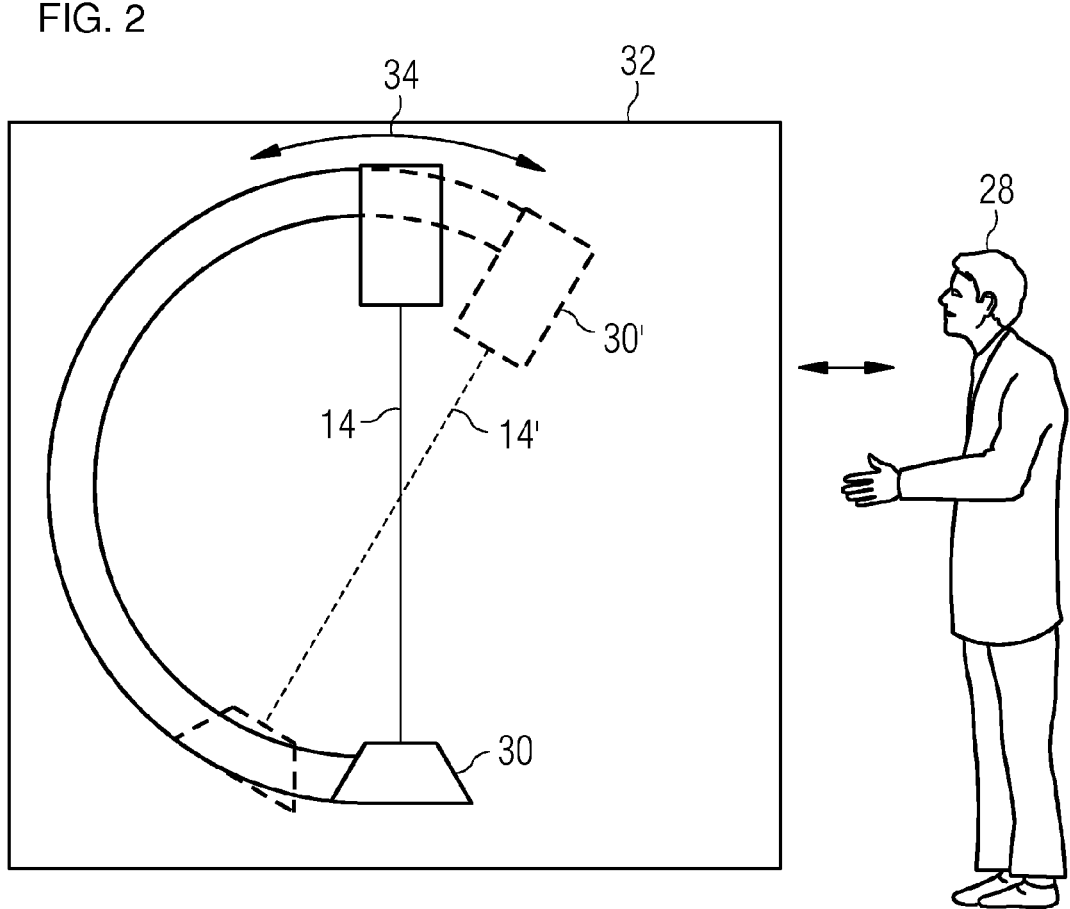
FIG. 2 is a side-elevational view of an exemplary representation on a monitor of outputting a measure for the deviation to a user.

FIG. 2 shows, by way of example, how the measure M for the deviation is output through a user interface to a user 28 and made visible on a monitor 32. Both the currently set position and orientation 30 of the X-ray machine and the location of the central ray 14 as well as the desired position and orientation 30' of the X-ray machine and the location of the central ray 14', are graphically displayed on the monitor 32. Likewise displayed are a displacement and rotation direction 34 necessary for setting the desired position and orientation 30' of the X-ray machine and the location of the central ray 14.

In an alternative embodiment, the X-ray machine 2 is motor-adjustable. The control and evaluation unit 26 outputs the measure M for the deviation, e.g. an angle α, as a control signal and the X-ray machine 2 is placed automatically.

In another embodiment, the location of the currently set central ray 14 is likewise indicated by a pointing element 16'. This is shown in dashed-line form in FIG. 1. For this purpose, the pointing element 16' is placed in such a way that the pointing line 18' indicated by the pointing element 16' coincides with the location of the currently set central ray 14. The acquisition unit 11 then records the location of the pointing line 18'. The control and evaluation unit 26 determines the measure M for the deviation between the currently set location of the central ray 14 and the desired location of the central ray 14' from the location of the pointing line 18' and the location of the pointing line 18.

The invention claimed is:

1. A method for producing an X-ray projection image of a body region of a patient using a desired spatial location of a central ray, the method comprising the following steps:

positioning a pointing element relative to the patient to indicate a location of a pointing line as the desired location of the central ray;

recording the location of the pointing line and a location of the central ray currently set on an X-ray machine;

measuring the deviation between the location of the pointing line and the currently set location of the central ray of the X-ray machine and calculating a spatial difference value between the current location and the desired location of the central ray; and positioning the X-ray machine so that the central ray coincides with the pointing line.

2. The method according to claim 1, which further comprises outputting the measure for the deviation to a user through a user interface.

3. The method according to claim 1, which further comprises outputting the measure for the deviation to the X-ray machine as a control signal and adjusting the X-ray machine by motor.

4. The method according to claim 1, which further comprises indicating the currently set location of the central ray with the pointing element.

5. The method according to claim 1, which further comprises moving the pointing element manually relative to the patient.

6. The method according to claim 1, which further comprises visually indicating the desired location of the central ray.

7. The method according to claim 1, which further comprises optically acquiring the currently set location of the central ray and the location of the pointing line.

8. A medical apparatus for producing an X-ray projection image of a body region of a patient using a desired spatial location of a central ray, the medical apparatus comprising:

an X-ray machine configured to take an X-ray projection image along the central ray;

a pointing element configured to indicate a pointing line;

an acquisition unit configured to record a location of the pointing line and a currently set location of the central ray; and a control and evaluation unit configured to implement software programmed to carry out the method according to claim 1.

9. The medical apparatus according to claim 8, wherein said X-ray machine is a C-arm-X-ray machine.

10. The medical apparatus according to claim 8, wherein said pointing element is pencil-shaped.

11. The medical apparatus according to claim 8, wherein said acquisition unit is mounted on the X-ray machine.

12. The medical apparatus according to claim 8, wherein said acquisition unit has an acquisition area encompassing a projection area of the X-ray machine.

13. The medical apparatus according to claim 8, wherein said acquisition unit is a camera.

14. The medical apparatus according to claim 8, wherein said acquisition unit operates in the visible light region.

15. The medical apparatus according to claim 8, wherein said acquisition unit has a plurality of sub-units with acquisition areas at least partially overlapping each other.

\* \* \* \* \*